(12) United States Patent
Kong

(10) Patent No.: US 6,210,360 B1
(45) Date of Patent: Apr. 3, 2001

(54) FLUID DISPLACEMENT PUMPS

(76) Inventor: Carl Cheung Tung Kong, 6122 Whittier Blvd., Los Angeles, CA (US) 90022

( * ) Notice: Subject to any disclaimer, the term of this patent is extended or adjusted under 35 U.S.C. 154(b) by 0 days.

(21) Appl. No.: 09/318,375

(22) Filed: May 26, 1999

(51) Int. Cl.$^7$ ................................................. A61M 1/06
(52) U.S. Cl. ............................. 604/73; 604/74; 604/315; 604/320
(58) Field of Search ......................... 604/74, 75, 76, 604/73, 315, 320, 322, 118, 119, 121, 346

(56) References Cited

U.S. PATENT DOCUMENTS

| | | |
|---|---|---|
| 4,705,504 | 11/1987 | Viers . |
| 4,892,517 | 1/1990 | Yuan et al. . |
| 4,961,726 | 10/1990 | Richter . |
| 5,358,476 | 10/1994 | Wilson . |
| 5,749,850 | * 5/1998 | Williams et al. ................. 604/74 |

* cited by examiner

Primary Examiner—Glenn K. Dawson
Assistant Examiner—Jennifer Maynard
(74) Attorney, Agent, or Firm—Kelly Bauersfeld Lowry & Kelley, LLP (57) ABSTRACT

A fluid displacement pump includes a rigid hollow body having a first open end, a flexible partition disposed within the hollow body adjacent the first open end to create a variable volume fluid chamber between the partition and the hollow body, and an actuator acting upon the flexible partition. A movable piston including a shaft connected to the actuator and a head connected to the partition may be disposed within the hollow body. The rigid housing acts as a guide for the piston head. A piston stop may be provided for limiting the movement of the piston. Further, a movable mass may be disposed within the hollow body and controlled by either a linear motor or a pulley system.

9 Claims, 11 Drawing Sheets

FLUID DISPLACEMENT PUMPS

BACKGROUND OF THE INVENTION

The present invention relates to fluid displacement pumps, and more particularly to fluid displacement pumps which utilize a low-friction flexible partition within a rigid hollow body.

There are a great number and variety of pumps in the art. The typical purpose of a pump is to move air or liquid from one location or container to another. Generally, a piston is movable within the pump to create a negative pressure or vacuum which moves the fluid from one location to the other. Pumps can be manually actuated or connected to a mechanical device. One of the problems associated with prior art pumps is that they have typically produced a tremendous amount of friction between the piston and the cylinder in which the piston moves. This limits the efficiency of the pump and increases running costs.

Although the surfaces of the piston and cylinder can be lubricated, this is not acceptable in all applications. For example, in a nursing breast pump the extracted milk should be as pure as possible so as not to adversely affect the baby. Hand pumps which do not have lubricated pump surfaces exist, but they take longer to extract an adequate amount of milk due to the friction which must be overcome while pumping.

Therefore, what is needed is a pump which significantly reduces the friction between moving parts without the use of a lubricant. What is further needed is a pump which is capable of pumping greater volumes than existing pumps of comparable size. The present invention fulfills these needs and provides other related advantages.

SUMMARY OF THE INVENTION

The present invention resides in a fluid displacement pump comprising, generally, a rigid hollow body having first and second open ends, a flexible partition disposed within the hollow body adjacent to an open end, and an actuator acting upon the partition to define a variable volume chamber between the partition and the hollow body. The flexible partition is preferably comprised of a low-friction elastomeric material. In several embodiments, a piston having a shaft connected to the actuator and a head connected to the flexible partition is utilized. The rigid housing acts as a guide for the piston and a piston stop may be connected to the hollow body to limit the movement of the piston in these embodiments.

In a first illustrated embodiment of the invention, the fluid displacement pump forms a nursing pump having a breast engaging cup in fluid communication with the first open end of the hollow body. The breast engaging cup may comprise an inverted elastomeric bottle nipple having a one-way valve through which extracted milk enters the variable volume chamber. An elongated conduit may be used between the first open end of the hollow body and the breast engaging cup for convenience of the user. The actuator comprises a hand actuated pump handle which moves the piston and thus the partition. The nursing pump includes a pump handle guide member and stopper attached to the second open end of the rigid hollow body to limit the movement of the pump handle. The nursing pump may be configured such that a second hollow body also having first and second open ends and a flexible partition disposed within the second end of the second hollow body is inserted into the first open end of the first hollow body, and the breast engaging cup is attached to the first open end of the second hollow body such that actuation of the piston through the pump handle creates a negative pressure in both variable volume chambers for the extraction of milk into the variable chamber of the second hollow body.

In a second embodiment of the invention the actuator comprises a movable mass within the hollow body which movement is controlled by a linear motor associated with the hollow body. Fluid displacement bodies comprising a housing having first and second open ends and a flexible partition joined to the housing are disposed within the hollow body adjacent to an end thereof.

In a third embodiment a moveable mass is disposed within the hollow body and is cooperatively controlled by a pulley system connected to the hollow body and a pivot which supports the hollow body. At least one fluid displacement body comprising a housing having first and second open ends and a flexible partition disposed therein and joined to the housing near the first end of the housing, is disposed within the hollow body adjacent the respective first and second opposing open ends. A fluid transfer member in fluid communication with the second open end of the housing of the fluid displacement body has a flexible partition joined to a wall thereof to create a variable volume cavity.

In a fourth illustrated embodiment, the rigid hollow body includes closure members pivotally connected to each open end which are capable of closing and opening the respective open ends. When one open end is closed the contents of the fluid chamber move towards the opposing open end. This embodiment is intended to operate in a vacuum, such as outer space, which pressure differential would act as the actuator to move the variable volume fluid chamber.

In a fifth embodiment, the fluid displacement pump includes a second rigid hollow body connected to the first hollow body. A conduit fluidly interconnects the second end of the first hollow body and a second end of the second hollow body. The second hollow body has first and second open ends and a flexible partition disposed within the second hollow body connected adjacent to the first open end forming a variable volume fluid chamber within the second hollow body. The second hollow body also has a rigid head member attached to the flexible partition of the second hollow body and cutting elements pivotally connected to the second end of the second hollow body. The cutting elements are also connected to the rigid head member and close and open depending on the position of the rigid head member which is dictated by the movement of the flexible partition of the first hollow body.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 3:
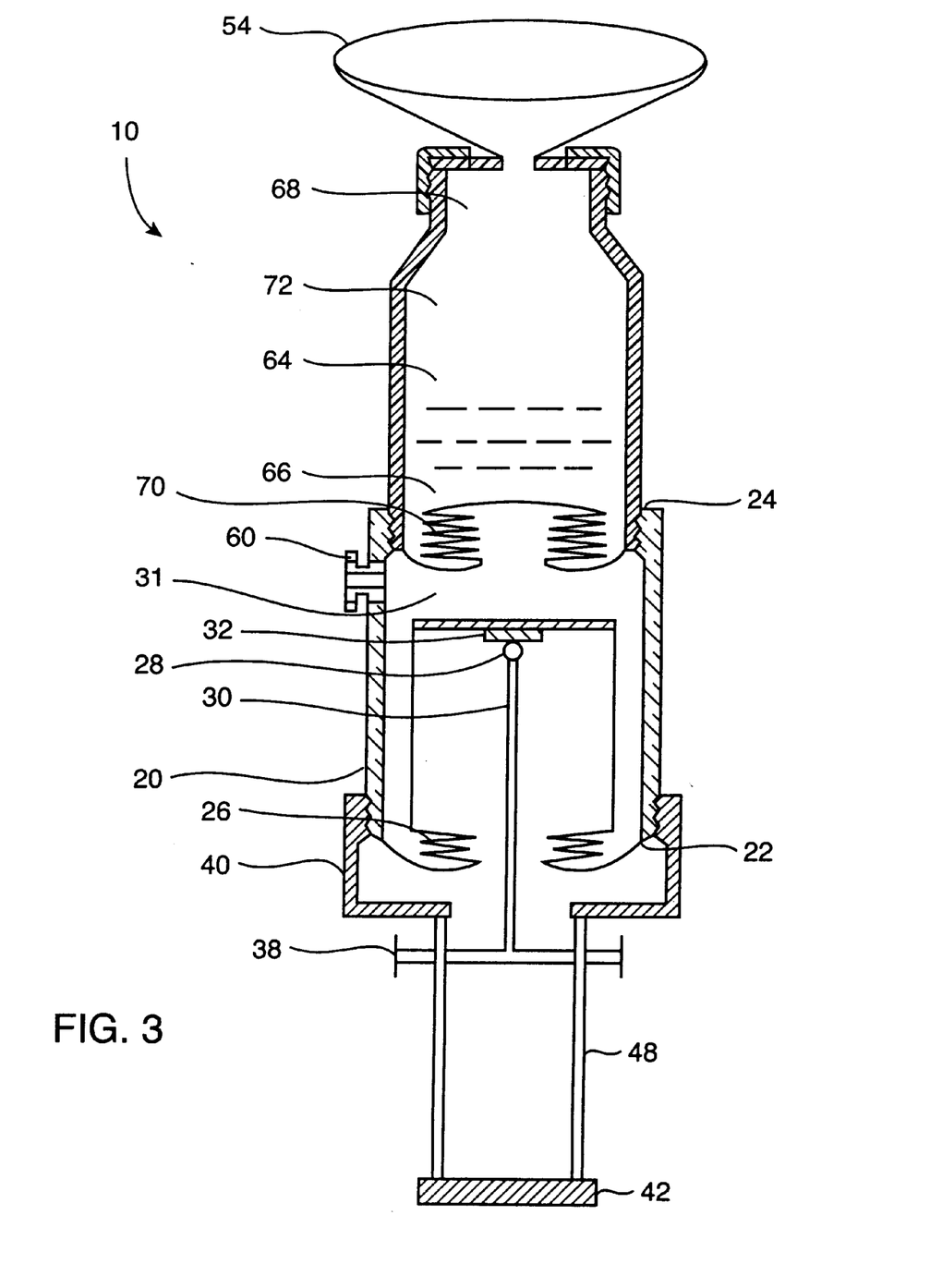
FIG. 3 is a cross-sectional view of another nursing fluid displacement pump having a horn shaped breast accepting cup and two rigid bodies attached to one another.
Figure 4:
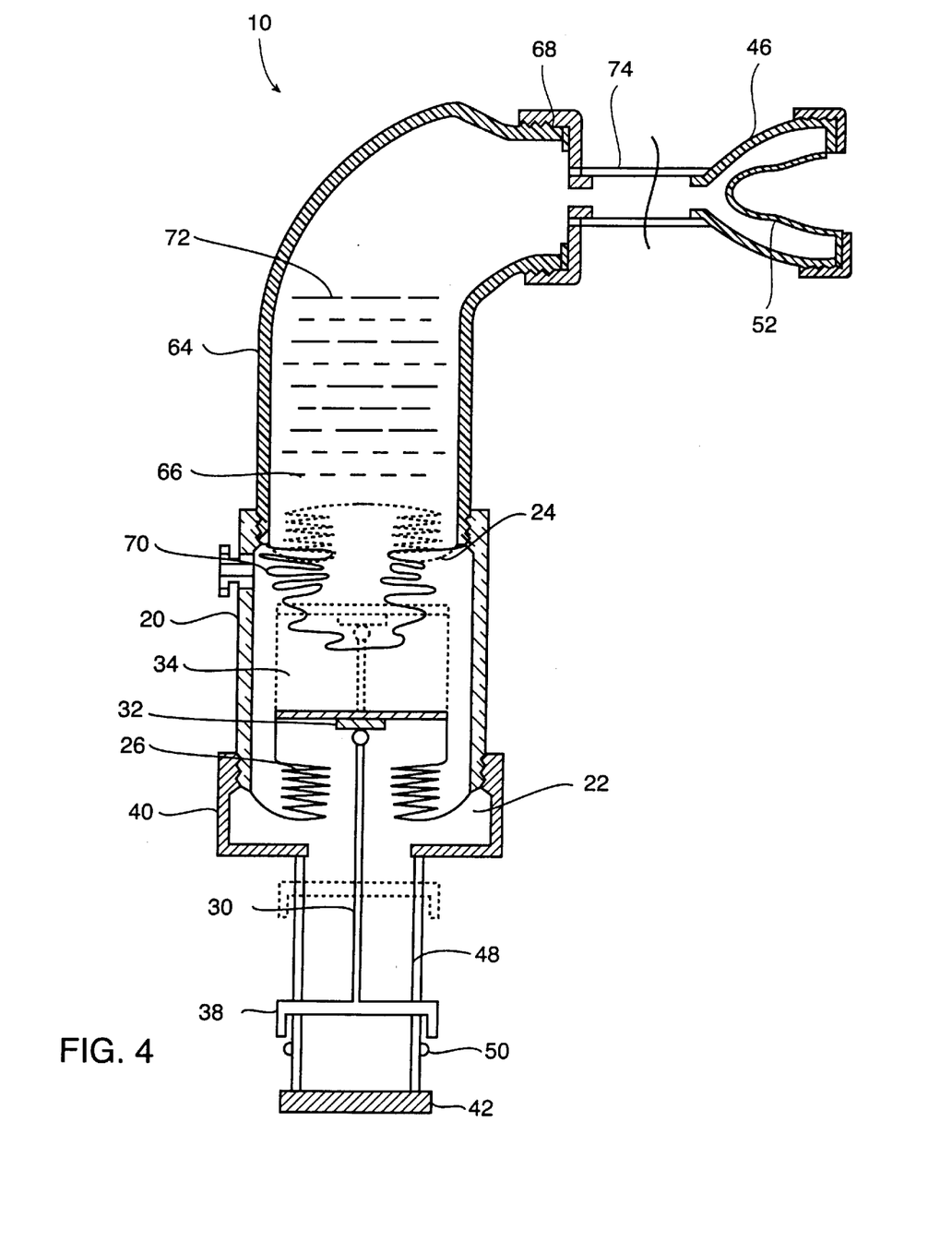
FIG. 4 is a cross-sectional view of a nursing fluid displacement pump similar to the nursing pump of FIG. 3, illustrating a conduit interconnected between an angled rigid body and a breast accepting cup.
Figure 5:
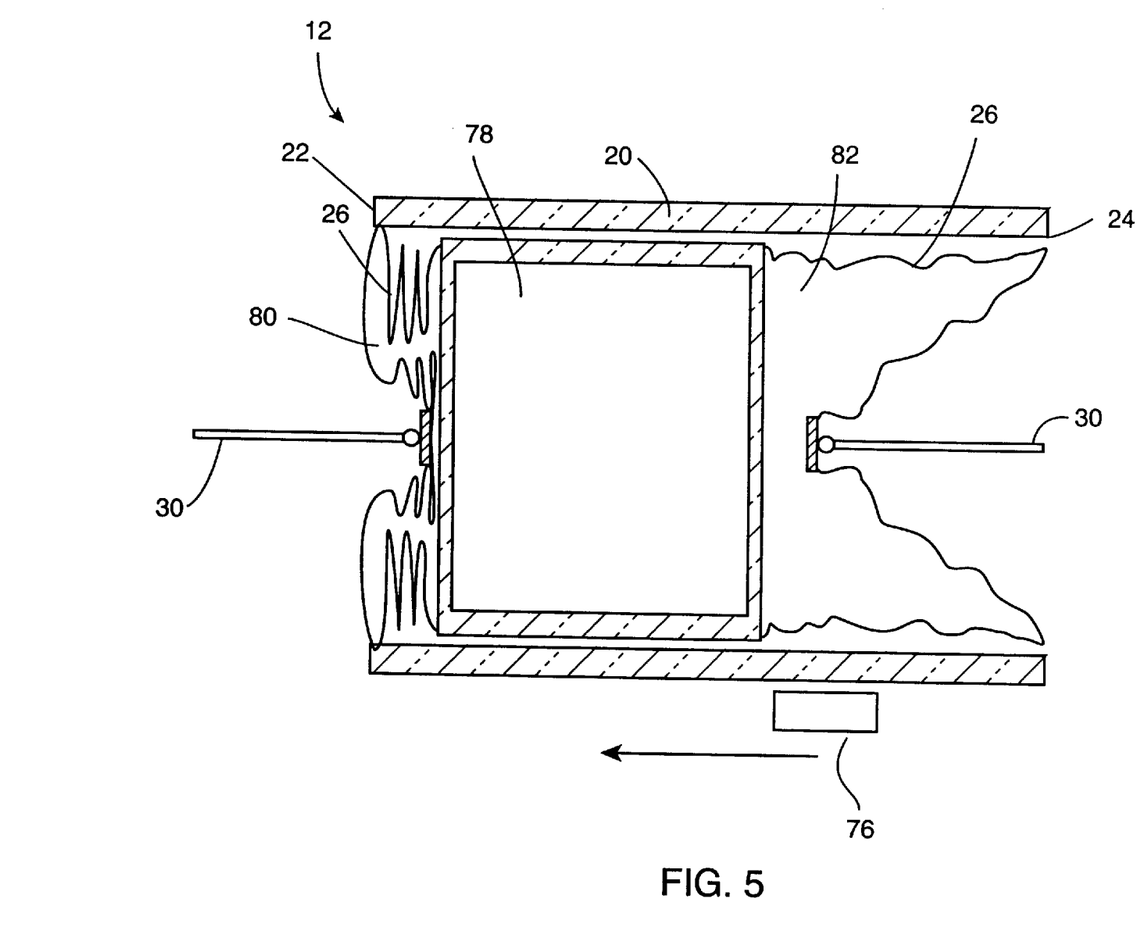
FIG. 5 is a cross-sectional view of a second embodiment of the present invention having a linear motor associated with the hollow body and a movable mass disposed within the hollow body.
Figure 6:
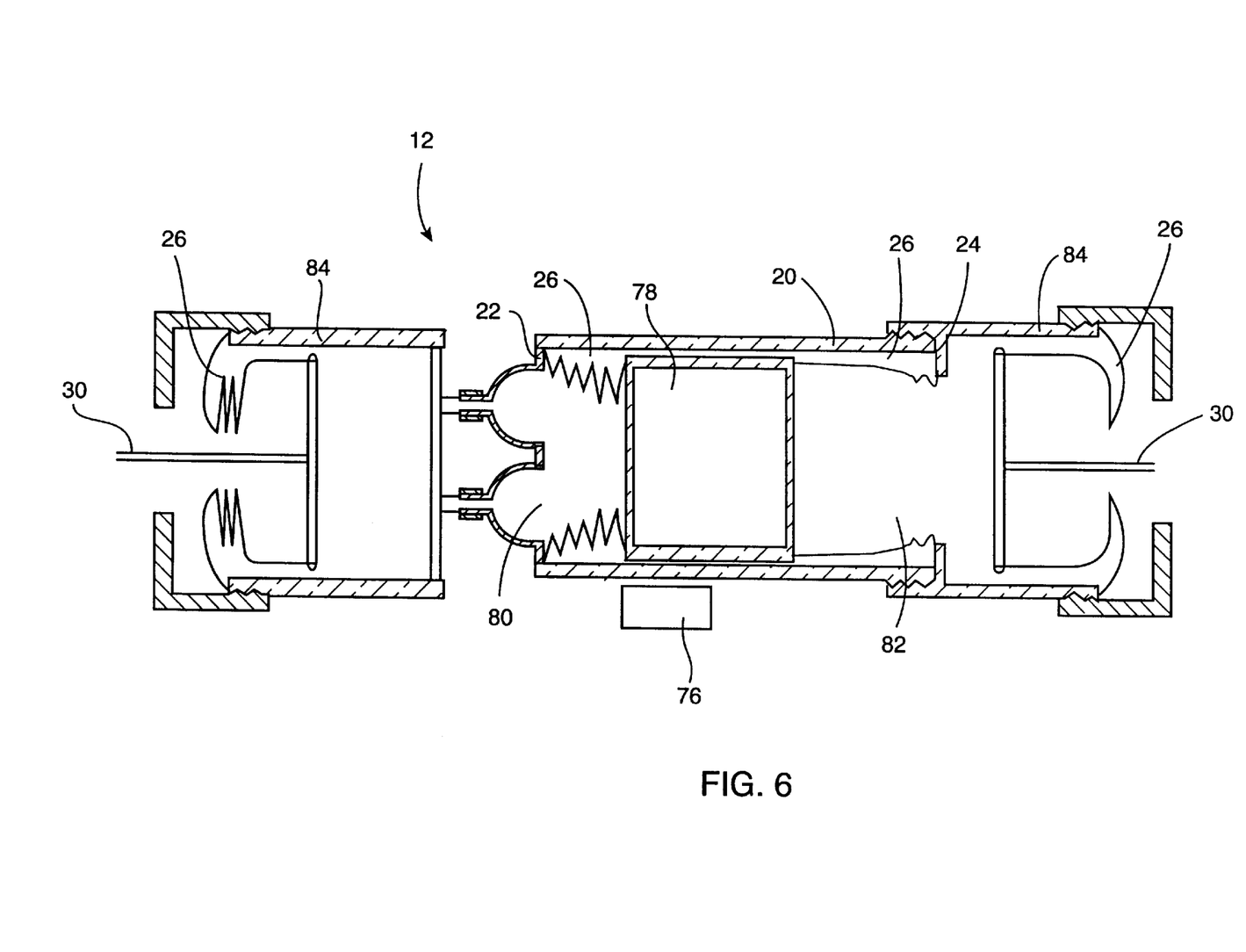
FIG. 6 is a cross-sectional view of a linear motor operated fluid displacement pump similar to the pump in FIG. 5, having fluid displacement pump housings fluidly connected at both ends of the hollow body.
Figure 7:
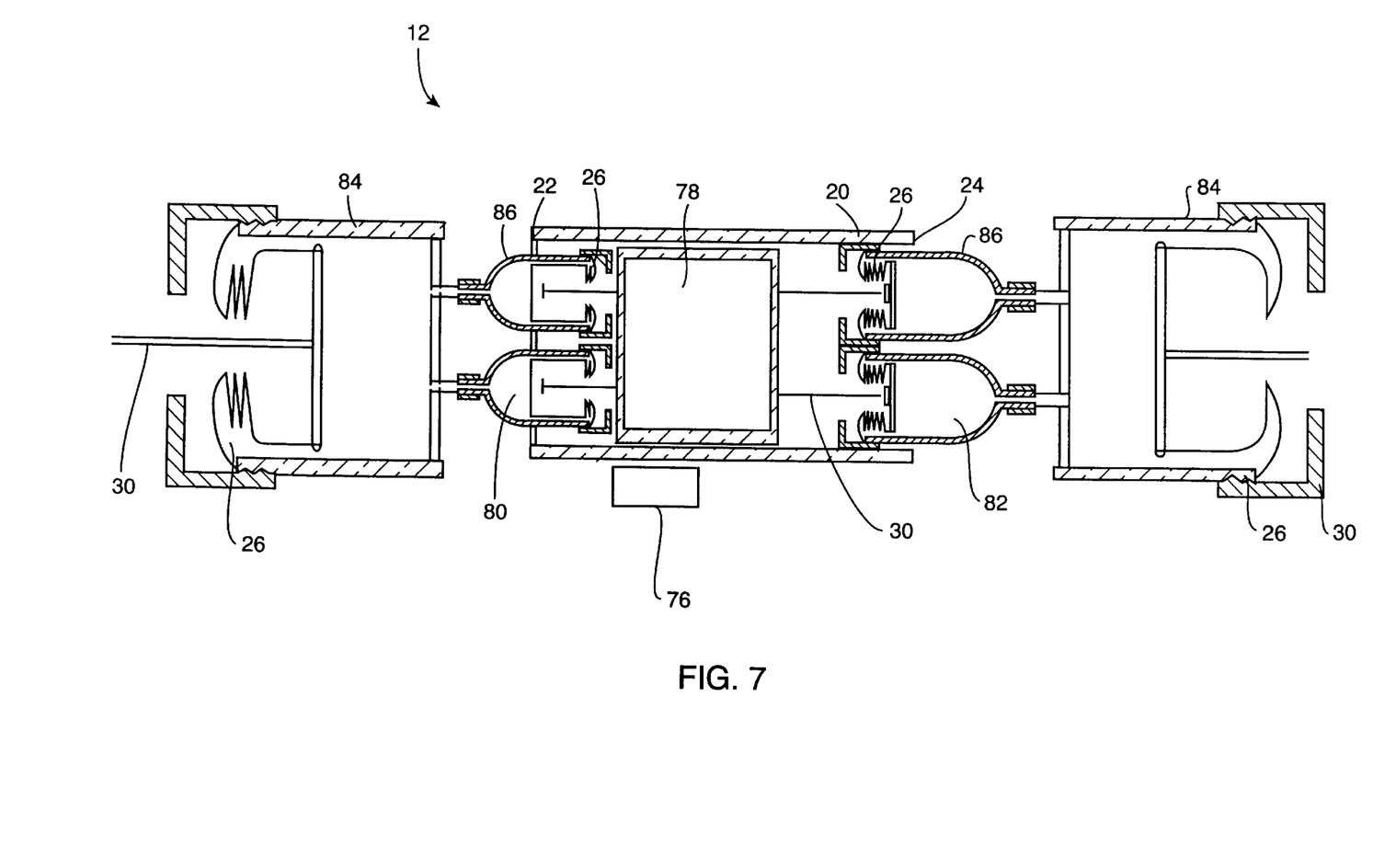
FIG. 7 is a cross-sectional view of another fluid displacement pump associated with a linear motor having multiple housings disposed within the hollow body and fluidly interconnecting the hollow body with the fluid displacement housings.
Figure 8:
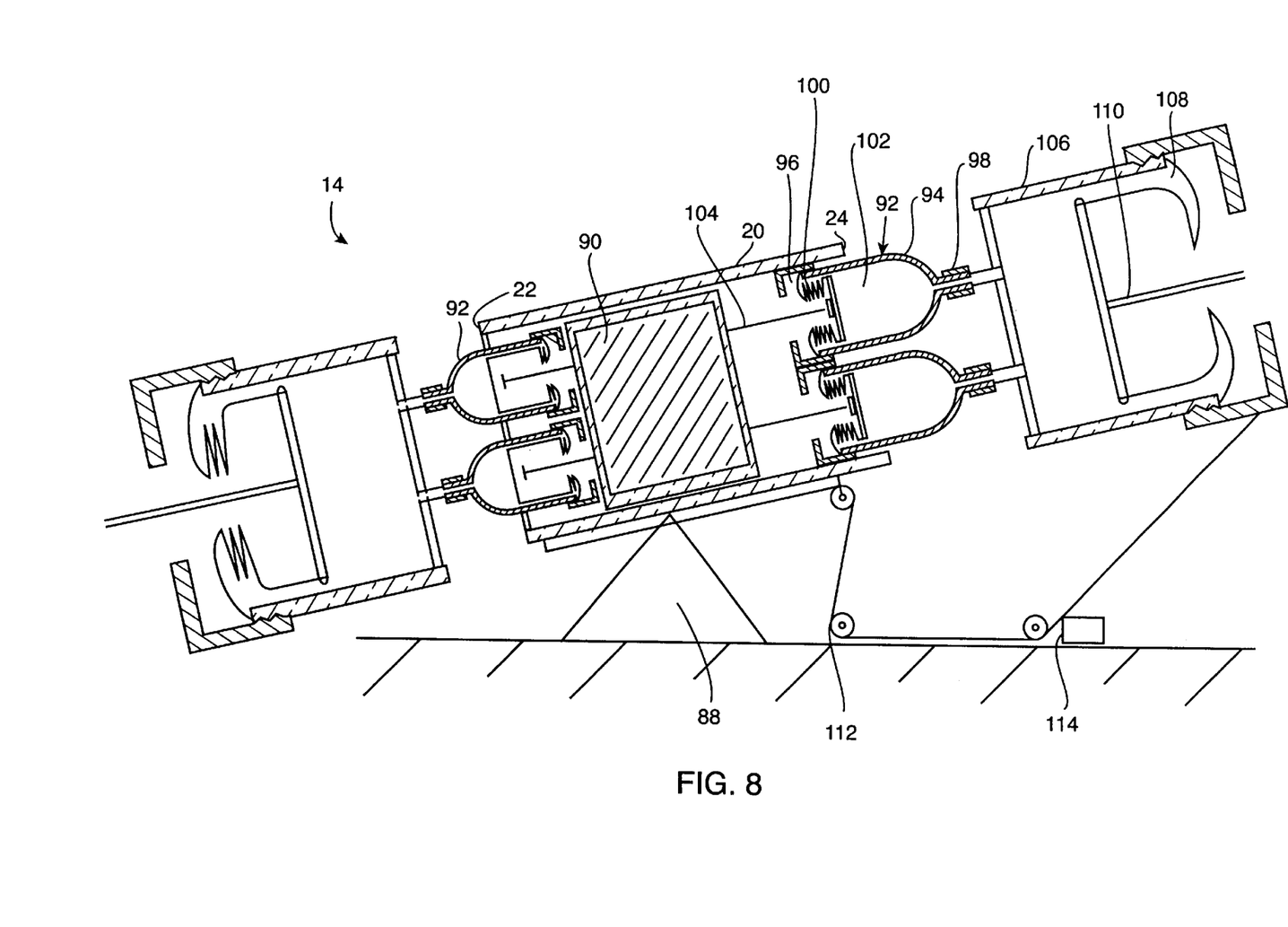
FIG. 8 is a cross-sectional view of a third embodiment of the fluid displacement pump of the present invention, illustrating a pivot supporting a hollow body having a slidable mass disposed therein and multiple fluid displacement bodies disposed within the hollow body and fluidly connecting the hollow body to fluid transfer members.
Figure 9:
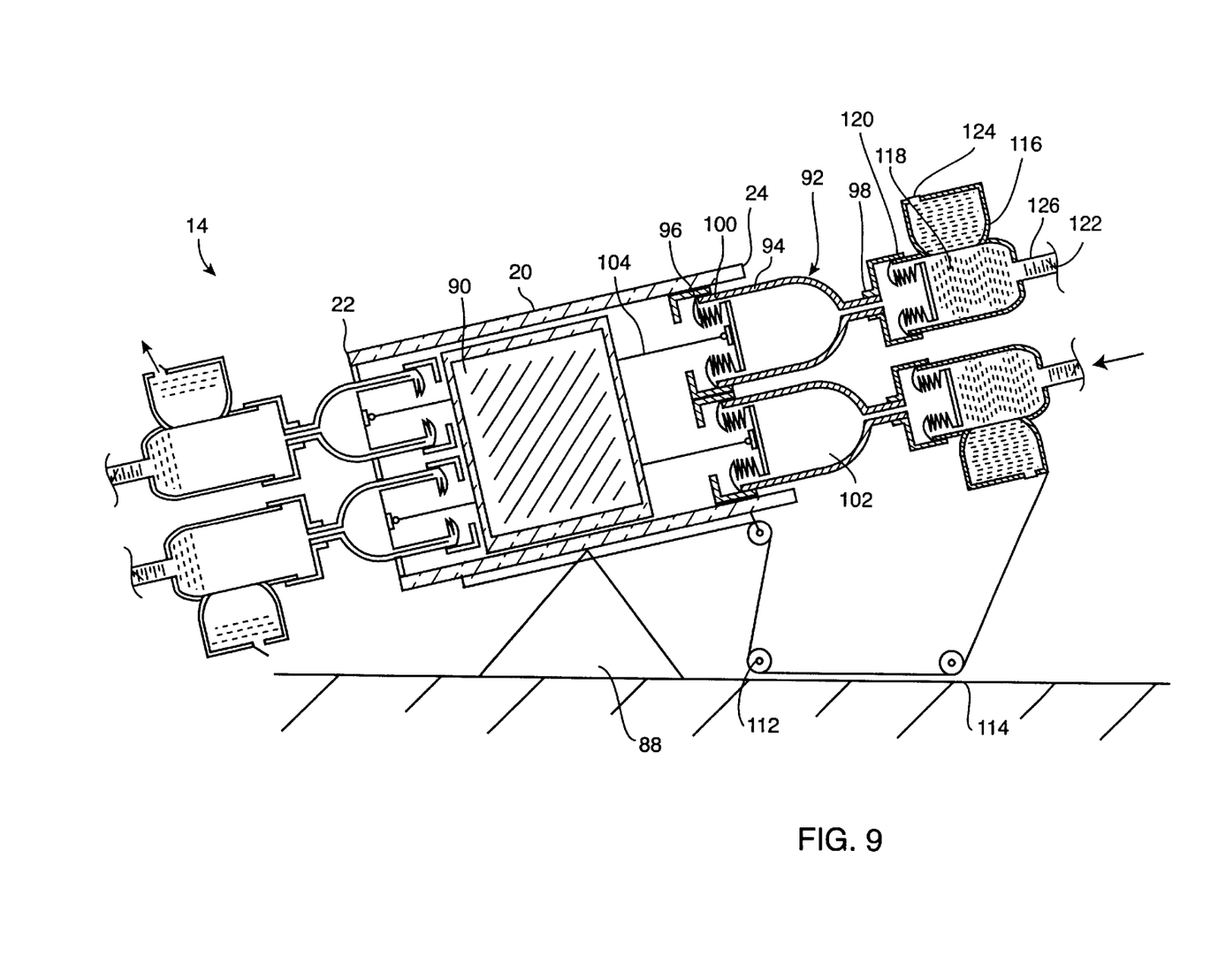
FIG. 9 is a cross-sectional view of the fluid displacement pump of FIG. 8 having fluid displacement reservoirs as fluid transfer members.
Figure 10:
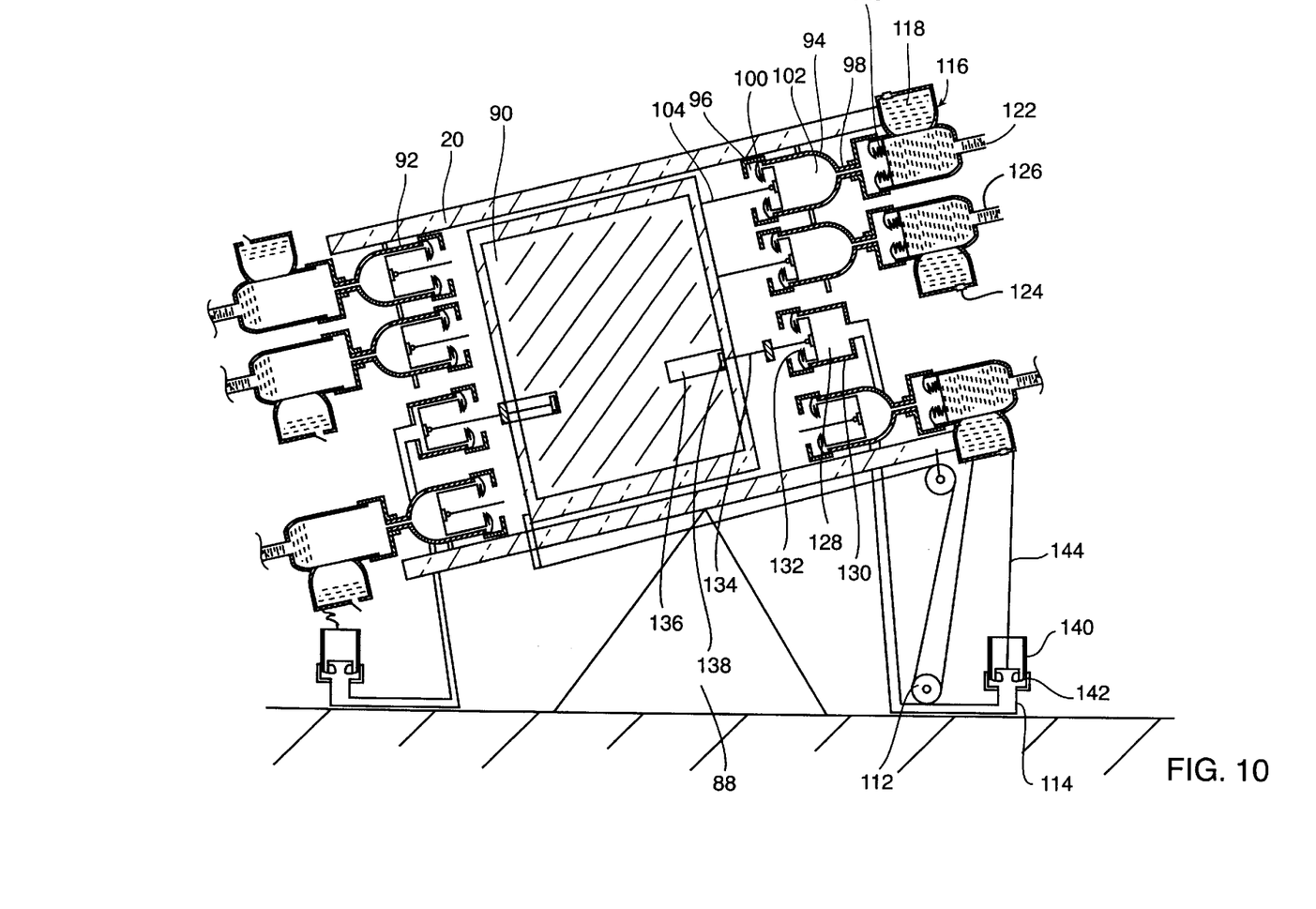
FIG. 10 is a cross-sectional view of a variation of the fluid displacement pump of FIG. 9.
Figure 11:
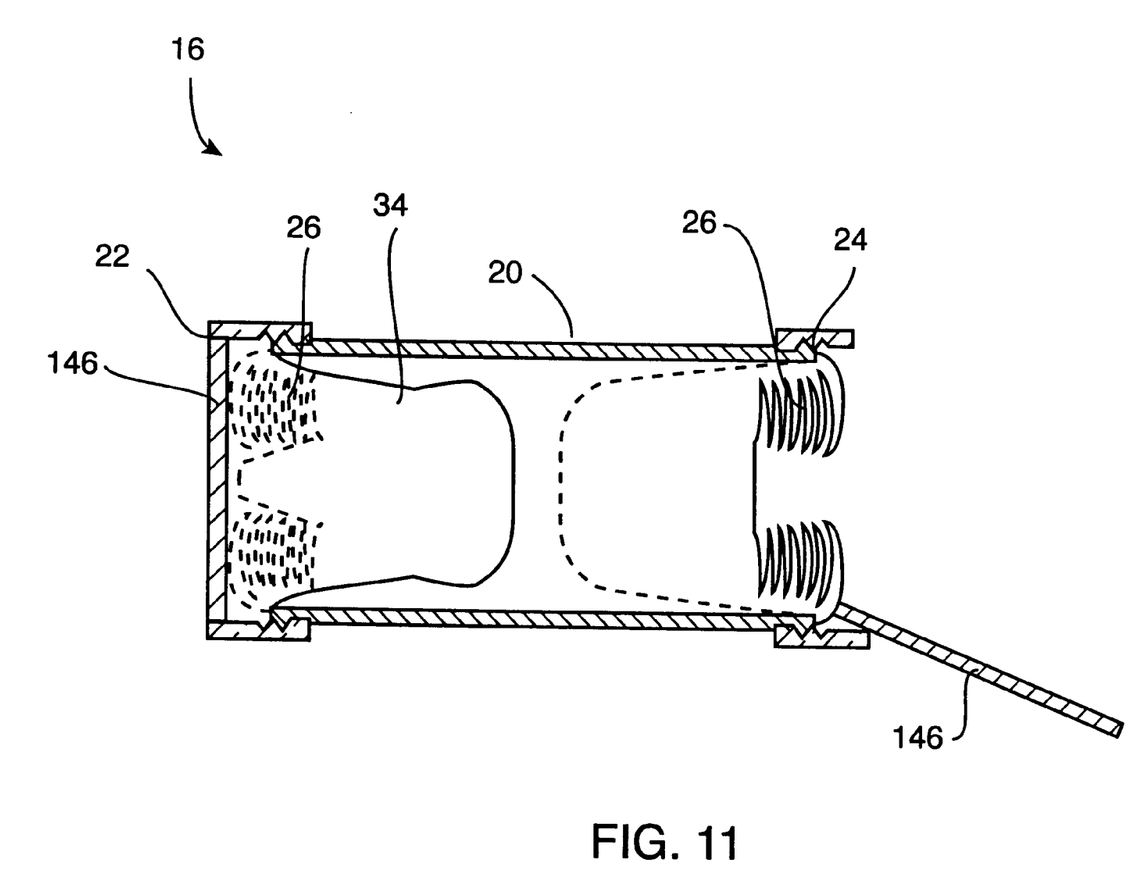
FIG. 11 is a cross-sectional view of a fourth embodiment of the fluid displacement pump of the present invention having pivotal closing members at each open end of the hollow body.
Figures 12, 13:
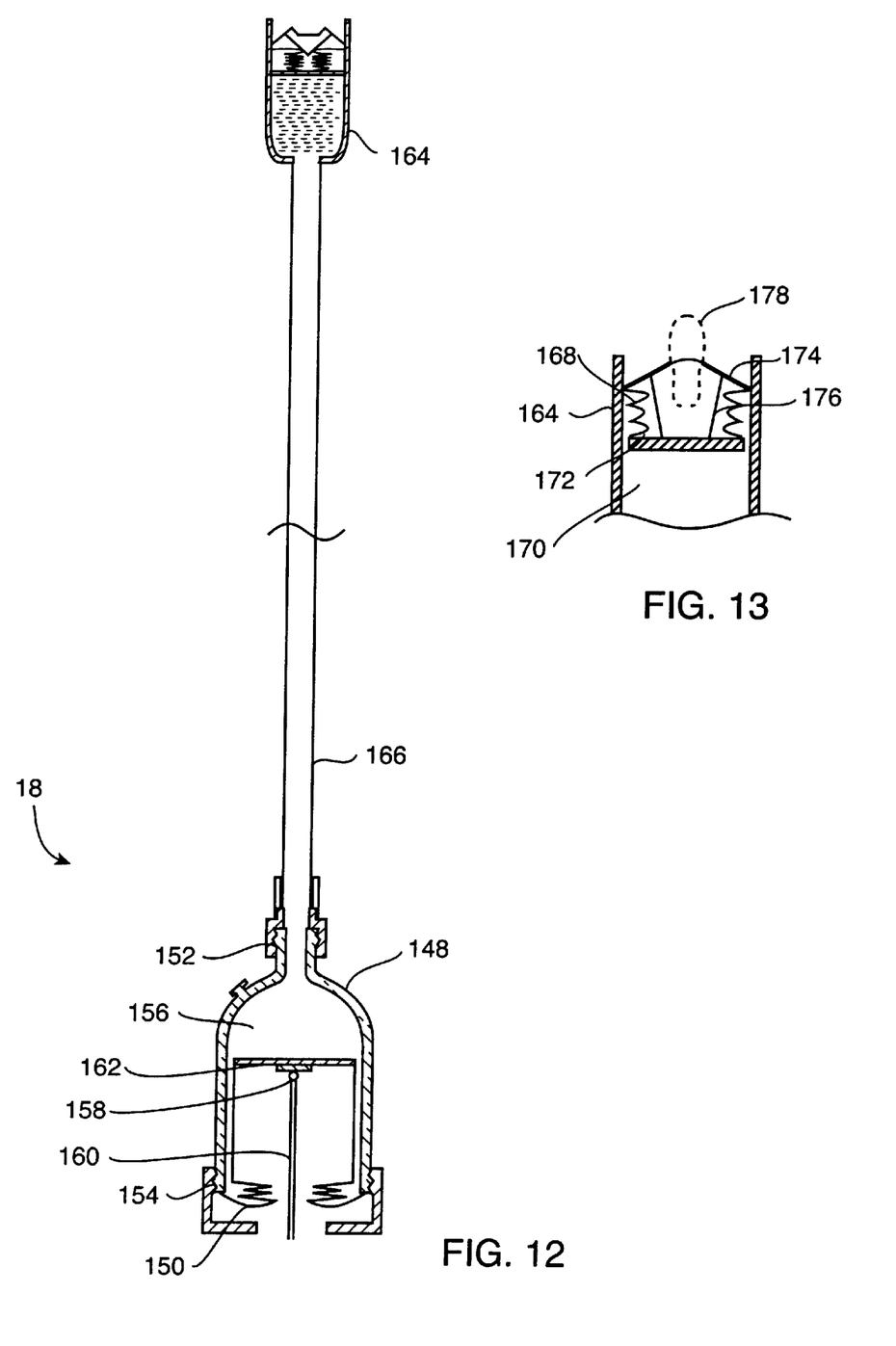
FIG. 12 is a cross-sectional view of a fifth embodiment of the fluid displacement pump of the present invention, illustrating two fluid displacement pumps in fluid connection with one another to activate cutting elements.
FIG. 13 is an enlarged cross-sectional view of the area designated by the number 13 in FIG. 12, illustrating the cutting elements cutting a phantom piece of tissue.

As illustrated in the accompanying drawings, a fluid displacement pump is generally referred to by the reference number 10 in FIGS. 1–4, by the reference number 12 in FIGS. 5–7, by the reference number 14 in FIGS. 8–10, by the reference number 16 in FIG. 11, and by the reference number 18 in FIGS. 12 and 13. The fluid displacement pumps 10–18 comprise, generally, a rigid hollow body 20 having opposing first and second open ends 22 and 24, a flexible partition 26 disposed within the hollow body 20 and substantially adjacent to either the first open end 22 and/or the second open end 24, a piston 28 disposed and movable within the hollow body 20 having a shaft 30 and head 32 which is connected to the partition 26 to define a variable volume chamber 34 between the hollow body 20 and the partition 26, and an actuator 34 acting upon the flexible partition 26. Moving the actuator 34 necessarily moves the piston 28 causing the flexible partition 26 to move back and forth from the first open end 22, creating a negative pressure, or vacuum-like effect, within the variable volume chamber 34. The partition 26 is preferably a low-friction elastomeric material so as to create a negative pressure within the fluid chamber 34 with as little friction and other opposing forces as possible in order to enhance the effectiveness and efficiency of the pumps 10–18.

Figure 1:
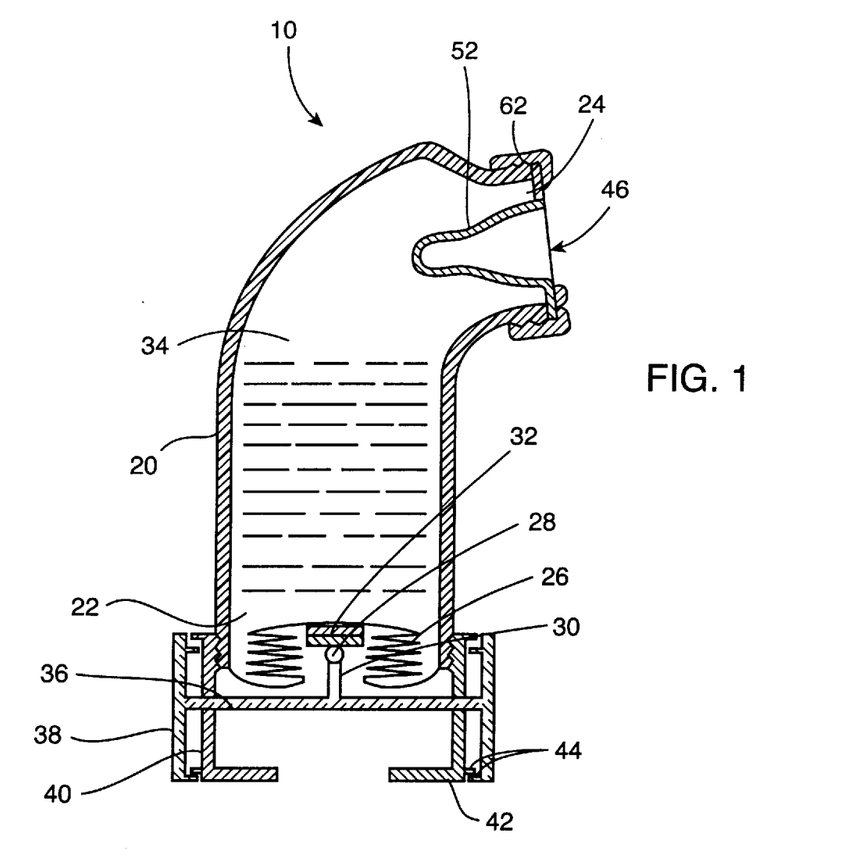
FIG. 1 is a cross-sectional view of a first embodiment of a nursing fluid displacement pump of the present invention, including an inverted nipple having a one-way valve.
Figure 2:
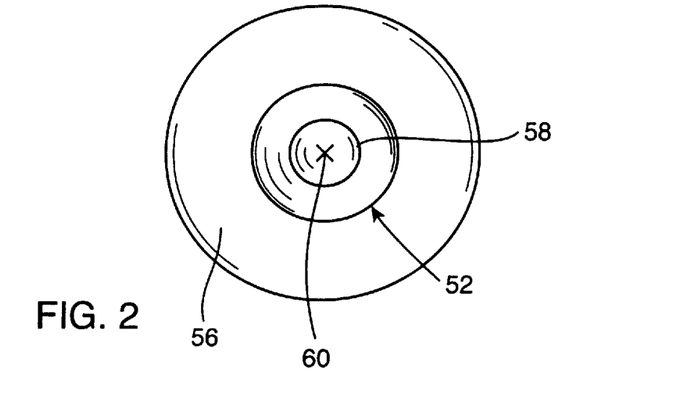
FIG. 2 is an end view of the nipple of FIG. 1.

Referring to FIGS. 1–4, a first embodiment of the fluid displacement pump in the form of a nursing pump 10 is shown. The flexible partition 26 of the nursing pump 10 is disposed within the hollow body 20 and may be connected to an inner surface of the hollow body 20 near the first opening 22, but is preferably removably disposed within the hollow body 20 with excess partition gathered near the first opening 22 as illustrated in FIG. 1. As shown in FIG. 3, a chamber accessing vacuum release valve may be formed through the hollow body 20 to release the negative pressure generated within the fluid chamber 34 during operation of the nursing pump 10.

The head 32 of the piston 28 is connected to the flexible partition 26. The piston shaft 30 is connected to an actuator 36 in the form of a manually actuated pump handle 38. A guide member 40 and a pump handle stopper 42 are attached to the first open end 22 of the hollow body 20. The guide 40 and stopper 42 can be of any form which will guide the pump handle 38 and limit its motion. A first exemplary form is illustrated in FIG. 1, wherein the pump handle 38 is cylindrical or semi-cylindrical and slidably fits over the guide member 40. Both the guide member 40 and the pump handle 38 have stoppers 42 in the form of protrusions 44 spaced from one another so as to allow the pump handle 38 to travel the space between the contact of the protrusions 44. A second exemplary form, as shown in FIGS. 3 and 4, also has a guide member 40 attached at the first open end 22 of the hollow body 20, but includes integrally formed railings 48 extending outwardly from the first open end 22 which guide the handle 38 to a stopper 42 at the terminus of the railings 48. The movement of the handle 38 towards the first open end 22 is limited by the inwardly disposed configuration of the guide member 40. An adjustable stopper 50 may be positioned on the railings 48 to further limit the travel of the pump handle 38, as illustrated in FIG. 4.

A breast accepting cup 46 is attached to the second open end 24. of the hollow body 20. The cup 46 may be in the form of an inverted elastomeric bottle nipple 52 as shown in FIG. 1, or in the form of a plastic horn 54 as shown in FIG. 3. As illustrated in FIG. 2, the nipple 52 has a relatively flat circular flange 56 from which arises a bulging, generally conically shaped head 58. A one-way valve 60 in the form of an x-shaped slit is formed at the apex of the nipple head 58. The nipple 52 is inverted head first into the second open end 24 of the hollow body 20 and a screw cap 62 fastens the flange 56 of the nipple 52 to the outer edge of the hollow body 20. As illustrated in FIG. 1, the rigid hollow body 20 may be bent or angled towards the second open end 24 aiding in the prevention of extracted milk spilling out of the second open end 24 and onto the user. The use of the one-way valve 60 allows the extraction of milk into the fluid chamber 34, but fully prevents the exit of extracted milk from the fluid chamber 34.

Another form of the nursing pump 10 is shown in FIGS. 3 and 4 which includes a second rigid hollow body 64 also having opposing first and second open ends 66 and 68 and a flexible partition 70 which creates a variable volume fluid chamber 72 within the second hollow body 64. The first open end 66 of the second hollow body 64 is securely inserted into the second open end 24 of the first hollow body 20. The breast accepting cup 46 is attached to the second open end 68 of the second hollow body 64. As illustrated in FIG. 4, the second hollow body 64 may be bent or angled near the second open end 68. A negative pressure or vacuum is created in the fluid chamber 72 of the second hollow body 64 by actuating the pump handle 38. Such movement of the flexible partition 26 of the first hollow body 20 creates a negative pressure within the fluid chamber 34 of the first hollow body 20 and acts upon the flexible partition 70 of the second hollow body 64. This in turn creates a negative pressure within the fluid chamber 72 of the second hollow body 64 and the extraction of milk into the fluid chamber 72.

This second form of the nursing pump 10 is useful as milk pumping sessions oftentimes produce more milk than one filled fluid chamber can hold. Therefore, the second hollow body 64 can be removed from the first hollow body 20 and another hollow body placed in the second hollow body's place. In this manner, multiple hollow bodies can act as milk storage devices, or even bottles if configured as such, without the immediate removal of the flexible partition 70 and insertion of another flexible partition.

As illustrated in FIG. 4, a flexible conduit 74 can interconnect a constricted second open end 24, 68 and the breast accepting cup 46. This allows the user to place the breast accepting cup 46 on the breast underneath clothes and actuate the pump 10 outside of the clothes. This is particularly useful in situations where private pumping is not convenient. The cup 46 may comprise the horn 54, nipple 52 or most preferably a nipple 52 having a one-way valve 60 within a horn 54 to prevent accidental milk spillage, as illustrated in FIG. 4.

Referring now to FIGS. 5–7, a second embodiment of the present invention is illustrated wherein the fluid displacement pump 12 is actuated by a linear motor 76 associated with the rigid hollow body 20. A linearly movable lightweight mass 78 is disposed within the hollow body 20. The movement and position of the lightweight mass 78 within the hollow body 20 is controlled by the linear motor 76. Preferably, the lightweight mass 78 comprises a hollow tube having a magnetic disc positioned within the tube or at an end thereof. The lightweight mass 78 is constructed to be as lightweight as possible to conserve energy applied to the linear motor 76. Flexible partitions 26 are disposed within the hollow body 20 and connected to the lightweight mass 78 to form first and second fluid cavities 80 and 82.

As illustrated in FIG. 5, the partitions 26 are also connected to the hollow body 20 adjacent the first and second open ends 22 and 24. Pistons 28 having elongated shafts 30 are connected to the flexible partitions 26 and as the lightweight mass 78 is moved from one open end of the hollow body 20 to the other open end, the shafts 30 are likewise moved due either to the compression of the contents of the fluid cavities 80 and 82 towards the shaft 30 or the negative pressure created when the lightweight mass 78 moves away from the partition 26 which causes the partitioned cavity 80 or 82 to move towards the lightweight mass 78. The shafts 30 may be connected to any useful device able to convert the movement of the shafts 30 into useful work. For example, an aluminum can manufacturing facility necessarily requires the lateral or vertical movement of shafts and heads to form the cylindrical cans from a sheet of metal.

A variation of the fluid displacement pump 12 using the linear motor 76 is illustrated in FIG. 6. The opposing first and second open ends 22 and 24 of the hollow body 20 are in fluid communication with second hollow bodies 84 having flexible partitions 26 which are connected to the shafts 30. The second hollow body 84 can be directly connected to an end of the hollow body 20, or interconnected with other members. In this manner, the movement of the lightweight mass 78 by the linear motor 76 towards the first open end 22 moves the fluid in the first fluid cavity 80 towards the shaft 30 thereby acting to move the shaft away from the lightweight mass 78 while creating a negative pressure in the second fluid cavity 82 and drawing that shaft 30 towards the lightweight mass 78.

Another variation of the linear motor operated fluid transfer pump 12 is illustrated in FIG. 7. Multiple housings 86 having flexible partitions 26 therein and shafts 30 interconnecting the lightweight mass 78 and the partitions 26 are used to transfer the fluid from the housings to the second hollow bodies 84 in order to move the shafts 30 of the second hollow bodies 84 in the same manner as described above. This variation is useful as the lightweight mass 78 is not exposed to the fluid.

Referring now to FIGS. 8–10, a third embodiment of a fluid displacement pump 14 utilizing a pivot point 88 is illustrated. The hollow body 20 is supported by a pivot point 88 and has a slidable heavy mass 90 disposed therein. Multiple fluid displacement bodies 92 are disposed within the hollow body 20 adjacent the open ends 22 and 24. The fluid displacement bodies 92 comprise housings 94 having opposing first and second opposing ends 96 and 98 and flexible partitions 100 joined adjacent the first open ends 96 to define variable volume fluid chambers 102 within the housings 94. Shafts 104 interconnect the partitions 100 and the slidable mass 90. The second open ends 98 of the housings 94 are fluidly connected to fluid transfer members 106 having flexible partitions 108 which are connected to shafts 110. A pulley system 112 is connected on points of the hollow body 20 on opposing sides of the pivot point 88, at least one of the fluid transfer members 106 and a pulley activating device 114.

The pump 14 operates by activating the pulley system 112 with the pulley activating device 114 which pulls a fluid transfer member 106 attached to the pulley system 112 downwardly causing the slidable mass 90 to slide towards that fluid transfer member 106. As the mass 90 moves towards the fluid transfer member 106, the shafts 104 of the fluid displacement bodies 92 push the fluid into the fluid transfer member 106, moving the shaft 110 away from the sliding mass 90. The pulley system 112 is then activated to pull the other fluid transfer member 106 downwardly resulting in the motion described above while pulling the shaft 110 of the ever extending upward fluid transfer member 106 towards the slidable mass 90. The use of low-friction materials in the composition of the slidable mass 90, partitions 100 and 108 and the placement of the hollow body 20 on the pivot point lessens the force applied to the pulley system 112 to operate the pump 14. Any useful device able to utilize the force created by the moving shafts 100 can be connected to the pump 14.

In a variation of this embodiment, as illustrated in FIG. 9, the second open end 98 of the fluid displacement bodies 92 are fluidly connected to reservoirs 116 having variable volume chambers 118 defined by flexible partitions 120. The reservoirs 116 include fluid inlet ports 122 and outlet ports 124 each having one-way valves 126 for the controlled flow of fluid into the reservoirs 116. Once again, the pulley system 112 is connected on points of the hollow body 20 on opposing sides of the pivot point 88, a reservoir 116 and a pulley activating device 114.

In operation, one set of reservoirs 116 are filled with fluid causing the slidable mass 90 to slide toward the end of the hollow body 20 which has the full reservoirs 116. This movement pushes the shafts 110 away from the mass 90 and displaces the fluid in the displacement bodies 92 towards the reservoirs 116 causing the partitions 120 to move into the reservoir 116. This force opens the outlet port one-way valve 126, releasing the fluid from the reservoir 116. Simultaneously, the shafts 104 on the opposite side of the sliding mass 90 are being pulled away from the reservoir 116 on that end, moving the partitions 120 of these reservoirs 116 toward the fluid displacement bodies 92, creating a negative pressure within the chambers 118 of the reservoirs 116. This negative pressure causes the inlet one-way valves 126 to open, filling the reservoirs 116 with fluid. So as one set of reservoirs 116 is emptying, the other set of reservoirs 116 are filling with fluid. The incoming fluid may be slightly pressurized to enhance this effect. The increasing weight in the reservoirs 116 filling levels the hollow body 20 until the slidable weight 90 slides towards the now completely filled reservoir chambers 118. This process is repeated with the pulley activating device 114 activating the pulley system 112 as needed to overcome friction and gravity to keep the pump 14 operating.

Yet another variation of this embodiment, as illustrated in FIG. 10, uses the same components as the variation above, but incorporates a fractionated pump displacement body 128 on either side of the pivot point 88. The fractionated pump displacement body 128 comprises a housing 130 of a predetermined fraction of the size of the surrounding fluid displacement bodies 92. The housing 130 has a flexible partition 132 which is connected to a shaft 134 which is further slidably connected to a channel 136 formed in the sliding mass 90. The movement of the shaft 134 within the channel 136 is limited not only by the length of the channel 136, but also stoppers 138 positioned on the shaft 134. The housing 130 is fluidly connected to a second housing 140 also having a flexible partition 142 although this partition 142 is connected via a cable 144 to an adjacent reservoir 116.

As the mass 90 slides towards the filled reservoirs 116, the shafts 104 of the fluid displacement bodies 92 are moved. However, the shaft 134 and thus the partition 132 of the housing 130 is not moved until a stopper 138 encounters the mass 90. As the partition 132 is moved away from the mass 90, fluid pushes the partition 142 of the second housing 140 upwardly towards the reservoir 116, loosening the cable 144. Simultaneously, just the opposite is occurring on the opposite side of the mass 90. The shaft 134 of the first housing 130 pulls the partition 132 of the first housing 130 towards the mass 90, filling the first housing 130 with the fluid from the second housing 140. As the fluid is displaced, the partition 142 of the second housing 140 moves downwardly away from the reservoir 116 tightening the cable 144 until the reservoir 116 itself begins to be pulled downwardly. This aids the downward movement of the filling reservoirs 116 so that the mass 90 more easily slides towards the reservoirs 116 when they are filled. It is intended that the use of the fractionated housings 130 lessens the activation needed by the pulley system activating device 114.

Referring specifically now to FIG. 11, a fourth embodiment of the fluid displacement pump 16 of the present invention is illustrated. This particular embodiment is intended to operate in a vacuum, such as outer space. The rigid hollow body 20 has a first and second open end 22 and 24 and partitions 26 disposed within the hollow body 20 adjacent to the open ends 22 and 24. A variable volume fluid chamber 34 is created between the partitions 26 and the hollow body 20. At either end of the hollow body 20 are closure members 146 which are constructed to seal off an open end 22 or 24. It is intended that when one of the closure members 146 seals off an open end, say for example the first open end 22, the fluid in the chamber 34 will flow towards the second open end 24 exposed to the outer vacuum. Before the fluid can reach the second open end 24, it is sealed by a closure member 146 and the first end 22 is opened. The force of the back and forth flowing of the fluid within the chamber 34 can be captured as energy and used in various devices.

A fifth embodiment of the fluid displacement pump 18 is illustrated in FIGS. 12 and 13. The pump 18 is comprised of a first rigid hollow body 148 having first and second open ends 150 and 152 and a flexible partition 154 disposed within the first hollow body 148 and connected thereto adjacent the first open end 150 to form a variable volume fluid chamber 156 within the first hollow body. A movable piston 158 having a shaft 160 and a head 162 attached to the flexible partition 154 is disposed within the first hollow body 148. The second open end 152 of the first hollow body 148 is fluidly connected to a first end 162 of a second hollow body 164 by a hollow conduit 166. The second hollow body 164 has a flexible partition 168 connected adjacent a second open end 170 of the second hollow body 164 and joined to a rigid head 172. Pivotally attached to the second open end 170 are cutting elements 174 which are also connected to the rigid head 172 by cables 176.

The fluid displacement pump 18 is intended to be used in the removal of internal tissue growths 178 such as polyps of the colon and hemorrhoids. Certain growths may spawn other growths if not completely removed from the body, such as cancer. Thus, it is important to remove all of the excised tissue 178 during the procedure. In use, the shaft 160 of the piston 158 is moved away from the second hollow body 164, and the fluid between the two hollow bodies 148 and 164 is pulled towards the first hollow body chamber 156. This movement causes the partition 168 and head 172 of the second hollow body 164 to move towards the first hollow body 148 as well. The cables 176 pull the cutting elements 174 inward towards the second open end 170 of the second hollow body 164. The cutting elements 174 cut the tissue 178 and pull the tissue 178 towards the vacancy left by the retreating rigid head 172 and partition 168. Under circumstances where the cutting elements 174 and tissue 178 form an airtight bond with the second opening 170, a vacuum effect is created to hold the tissue 178 in place.

Although several embodiments have been described in detail for purposes of illustration, various modifications may be made to each without departing from the scope and spirit of the invention. Accordingly, the invention is not to be limited, except as by the appended claims.

What is claimed is:

1. A fluid displacement pump, comprising:

a rigid hollow body having first and second open ends;

at least one fluid displacement body comprising a housing having first and second open ends and a flexible partition joined to the housing near a first end thereof, the at least one displacement body being disposed within the hollow body adjacent to an end thereof;

a pivot supporting the hollow body between the first and second ends thereof;

a flexible partition of a low-friction elastomeric material disposed within the hollow body adjacent to at least one of the open ends;

an actuator comprising a mass movable within the hollow body and substantially conforming to an inner surface of thereof and which acts upon the flexible partition so as to move the partition within the hollow body, creating a variable volume fluid chamber between the partition and the hollow body; and a pulley system having cables connected to the hollow body on each side of the pivot for aiding the movement of the mass within the hollow body.

2. The displacement pump of claim 1, wherein the actuator comprises a closure member connected to the hollow body at an end thereof, the closure member periodically closing and opening the open end of the hollow body to cause the fluid chamber to move within the hollow body.

3. The displacement pump of claim 1, including a fluid transfer member in fluid communication with the second end of the housing of the displacement body, and a flexible partition joined to a wall of the fluid transfer member to create a variable volume cavity therein.

4. The displacement pump of claim 1, including a piston having a shaft connected to the actuator and a head connected to the flexible partition, and a piston stop connected to the hollow body, wherein the rigid hollow body acts as a guide for the piston.

5. A fluid displacement pump, comprising:

a rigid hollow body having first and second open ends;

a flexible partition of a low-friction elastomeric material disposed within the hollow body adjacent to at least one of the open ends;

multiple fluid displacement bodies each comprising a housing having first and second open ends and a flexible partition joined to the housing near a first end thereof, the displacement bodies being disposed within the hollow body adjacent to an end thereof;

a piston having a head connected to the flexible partition, and a shaft extending therefrom, the piston being guided by the rigid hollow body; and an actuator comprising a mass substantially conforming to an inner surface of the hollow body and movable within the hollow body and which acts upon the flexible partition so as to move the partition within the hollow body, creating a variable volume fluid chamber between the partition and the hollow body.

6. The displacement pump of claim 5, wherein a linear motor associated with the hollow body controls the movement of the mass within the hollow body.

7. The displacement pump of claim 5, wherein the actuator comprises a mass moveable within the hollow body, and wherein a pivot supporting the hollow body and a pulley system connected to the hollow body cooperatively move the mass within the hollow body.

8. The displacement pump of claim 7, including at least one fluid displacement body comprising a housing having first and second open ends and a flexible partition joined to the housing near a first end thereof, the at least one displacement body being disposed within the hollow body adjacent an end thereof and further including a fluid transfer member in fluid communication with the second end of the housing of the displacement body and having a flexible partition joined to a wall of the fluid transfer member to create a variable volume cavity therein.

9. The displacement pump of claim 5, including a piston stop connected to the hollow body.

* * * * *